United States Patent
Zhong et al.

(10) Patent No.: US 11,492,668 B2
(45) Date of Patent: Nov. 8, 2022

(54) INDEL MOLECULAR MARKER CLOSELY LINKED TO PHOTOPERIOD INSENSITIVITY IN PUMPKINS AND APPLICATION THEREOF

(71) Applicant: VEGETABLE RESEARCH INSTITUTE, GUANGDONG ACADEMY OF AGRICULTURAL SCIENCES, Guangdong (CN)

(72) Inventors: Yujuan Zhong, Guangdong (CN); Hexun Huang, Guangdong (CN); Junxing Li, Guangdong (CN); Wenlong Luo, Guangdong (CN); Tingquan Wu, Guangdong (CN); Rui Wang, Guangdong (CN)

(73) Assignee: VEGETABLE RESEARCH INSTITUTE, GUANGDONG ACADEMY OF AGRICULTURAL SCIENCES, Guangdong (CN)

( * ) Notice: Subject to any disclaimer, the term of this patent is extended or adjusted under 35 U.S.C. 154(b) by 364 days.

(21) Appl. No.: 16/497,863

(22) PCT Filed: Nov. 1, 2018

(86) PCT No.: PCT/CN2018/113460
§ 371 (c)(1),
(2) Date: Sep. 26, 2019

(87) PCT Pub. No.: WO2019/128461
PCT Pub. Date: Jul. 4, 2019

(65) Prior Publication Data
US 2020/0199673 A1    Jun. 25, 2020

(30) Foreign Application Priority Data
Dec. 26, 2017   (CN) .......................... 201711432898.X

(51) Int. Cl.
*C12Q 1/6883*    (2018.01)
*C12N 15/10*    (2006.01)

(52) U.S. Cl.
CPC ....... *C12Q 1/6883* (2013.01); *C12N 15/1003* (2013.01); *C12Q 2600/13* (2013.01); *C12Q 2600/156* (2013.01)

(58) Field of Classification Search
CPC ............ C12N 15/1003; C12Q 2600/13; C12Q 2600/156; C12Q 1/6895
See application file for complete search history.

(56) References Cited

FOREIGN PATENT DOCUMENTS

| CN | 103305507 A | 9/2013 |
|----|-------------|--------|
| CN | 104869808 A | 8/2015 |
| CN | 108048595 A | 5/2018 |
| WO | 2016183005 A1 | 11/2016 |

OTHER PUBLICATIONS

Zhong et al. Scientific Reports. 2017. 7:12785. (Year: 2017).*
Esteras et al. BMC Genomics. 2012. 13:80. (Year: 2012).*
Sun et al. Molecular Plant. 2017. 10:1293-1306. (Year: 2017).*
Wu et al. Mol Breeding. 2014. 34:1437-1447. (Year: 2014).*
Molecular Marker Analysis of Photoperiod-insensitivity Genes in Oat; Journal of Triticeae Crops, Dec. 31, 2011.
H. Zhang, et al., Cucurbita moschata cultivar Rifu unplaced genomic scaffold, Cmos_1.0 Cmo_Scf00002, whole genome shotgun sequence; Karyotype Stability and Unbiased Fractionation in the Paleo-Allotetraploid Cucurbita Genomes; Mol Plant 10 (10), 1293-1306 (2017).

* cited by examiner

*Primary Examiner* — Joseph G. Dauner
(74) *Attorney, Agent, or Firm* — McNees Wallace & Nurick LLC

(57) ABSTRACT

The invention discloses an indel molecular marker closely linked with pumpkin photoperiod insensitivity and application of the indel molecular marker, and belongs to the technical field of molecule detection. The indel molecular marker SEQ7593 is located on a tenth chromosome of a *Cucurbita moschata*, and is 280 bp in size. The nucleotide sequence of the indel molecular marker is shown as SEQ ID NO: 1. The indel molecular marker SEQ7593 can be directly used for creating an assistant breeding system of photoperiod insensitivity character molecular markers. Primer amplification designed according to the Indel molecular marker can be applied to assistant breeding of pumpkin breed improvement molecules in a simple, rapid and high-throughput manner, technical support is provided for pumpkin photoperiod insensitivity molecular breeding, and time for conventional gene positioning is shortened greatly.

2 Claims, 3 Drawing Sheets
(2 of 3 Drawing Sheet(s) Filed in Color)
Specification includes a Sequence Listing.

INDEL MOLECULAR MARKER CLOSELY LINKED TO PHOTOPERIOD INSENSITIVITY IN PUMPKINS AND APPLICATION THEREOF

PRIORITY

The present application is U.S. National Stage Patent Application under 35 USC 371 which claims priority to Patent Cooperation Treaty Patent Application PCT/CN2018/113460, filed Nov. 1, 2018, which claims priority to and benefit of Chinese Application No. 201711432898.X, CN, filed Dec. 26, 2017, each with the title "INDEL MOLECULAR MARKER CLOSELY LINKED TO PHOTOPERIOD INSENSITIVITY IN PUMPKINS AND APPLICATION THEREOF," each of which is hereby incorporated by reference in their entirety.

SEQUENCE LISTING

The instant application contains a Sequence Listing which has been submitted in ASCII format via EFS-Web and is hereby incorporated by reference in its entirety. Said ASCII copy, created Feb. 4, 2020, is named A7343749.txt and is 1,700 bytes in size.

TECHNICAL FIELD

The present invention belongs to the technical field of molecular detection, specifically relates to an Indel molecular marker closely linked to photoperiod insensitivity in pumpkins and application thereof.

BACKGROUND

*Cucurbita moschata* is one of the three major cultivars of pumpkin and ranking the first in yield and planting area among the three cultivars. However, *Cucurbita moschata* is a diclinous short-day plant, most of which have photoperiod and temperature sensitivity. In spring, the suitable sowing period in south China is short (from January to March), until April female flower differentiation decreases, leading to the severe reduction in yield. In China, the main varieties of *Cucurbita moschata* are restricted by planting area. For example, "Miben" and its derivatives are not suitable for planting in the north of the Yellow River. Thus, the photoperiod and temperature sensitivity greatly restricts the sowing time and geographical distribution of the *Cucurbita moschata*. In addition, flowering of the plants originated from tropical and subtropical regions is mainly affected by the photoperiod. Therefore, selective breeding of photoperiod insensitivity in *Cucurbita moschata* varieties has the broad application prospects.

Selective breeding of the photoperiod-insensitivity in varieties is difficult by the traditional breeding method. Generally, the screen in the long-day is time- and labor-consuming, which greatly affects the pumpkin breeding in China. However, with the maturity of high-throughput sequencing technology, especially developing a large number of SNP (Single base amplification polymorphism) markers and applying of high-density genetic map related method for precise mapping has become one of the hot spots for discovery of plant genes. Furthermore, based on the complete genome information of pumpkin, the period of breeding cycle would be greatly shortened and the breeding efficiency would be greatly improved by developing trait-linked Indel molecular markers for carrying out initial screen of the varieties to achieve the purpose of molecular-assisted breeding. Therefore, it is of great significance for the improvement to the gene with photoperiod insensitivity by carrying out pumpkin gene mapping which is photoperiod insensitive, screening closely-linked molecular markers and establishing molecular marker-assisted selection system in the early stage.

SUMMARY

An object of the present invention is to provide an Indel molecular marker closely linked to photoperiod insensitivity in pumpkins and application thereof.

To achieve the object, the present invention adopts the technical solutions as follows:

Through studies, the inventors performed QTL mapping of the photoperiod insensitivity in pumpkins, go with a closely linked molecular markers named as SEQ7593 through screening. The corresponding pumpkin would exhibit photoperiod insensitivity if the sequence is found as shown in SEQ ID NO: 1. The corresponding pumpkin would exhibit photoperiod sensitivity if the sequence as shown in SEQ ID NO: 1 is found the deletion of fragment TCATA, i.e. the deletion of the base fragment is 5 bp in size, which is the sequence from the 129th from the 5' to the 133th positions as shown in SEQ ID NO: 1 to obtain the one with 275 bp in size as shown in SEQ ID NO: 2

```
                                           (SEQ ID NO. 1)
TTTCAGCTCTTACCCTATTCTTCAGAGTGAAAACCTA

CCCTTCAATAATTGAAGCCTTAAACTTTAGAATTATT

AGAGATTCTTTAGAATGTTGGATAAAATTTAGTTCTG

AAATAGTGCCAAGTTTATCATACATATGTTCTATGTT

CTAAGTTCCATCCAAAATTCTAATTGTGCTCAAGAGT

AGTTTTGAAATTTTTGTGAAATATTGTAAATCTGATG

AGAATAGATGTATTATTAAAACAAATCTGATGAAGTC

CAAGTTAAGGAGTAAAATGTG.

(SEQ ID NO. 2)
TTTCAGCTCTTACCCTATTCTTCAGAGTGAAAACCTA

CCCTTCAATAATTGAAGCCTTAAACTTTAGAATTATT

AGAGATTCTTTAGAATGTTGGATAAAATTTAGTTCTG

AAATAGTGCCAAGTTTACATATGTTCTATGTTCTAAG

TTCCATCCAAAATTCTAATTGTGCTCAAGAGTAGTTT

TGAAATTTTGTGAAATATTGTAAATCTGATGAGAAT

AGATGTATTATTAAAACAAATCTGATGAAGTCCAAG.

TTAAGGAGTAAAATGTG.
```

The Indel molecular marker SEQ7593 closely linked to photoperiod insensitivity in pumpkins is located on *Cucurbita moschata* tenth chromosome and is 280 bp in size. Its nucleotide sequence is shown as in SEQ ID NO: 1; the corresponding Indel sequence thereof is found the deletion of a base fragment with 5 bp in size from the 129th to the 133th positions as shown in SEQ ID NO: 1.

A primer pair used for amplifying the Indel molecular marker SEQ7593 of claim 1 and/or corresponding Indel sequence thereof. A primer pair used for amplifying the above-mentioned Indel molecular marker SEQ7593.

Preferably, the nucleotide sequence of said primer pair is as follows:

```
F1: 5'-TTTCAGCTCTTACCCTATTCTTC-3',       (SEQ ID NO 3)

R1: 5'-CACATTTTACTCCTTAACTTGGAC-3'.      (SEQ ID NO. 4)
```

A kit used for assisted breeding of photoperiod insensitivity in pumpkins, comprises a reagent used for detecting the presence of TCATA deletion in said Indel molecular marker SEQ7593 of claim 1.

Further, the reagent comprises a primer pair for amplifying the Indel molecular marker SEQ7593 and/or corresponding Indel sequence thereof.

Further, a nucleotide sequence of the primer pair is as follows:

```
F1: 5'-TTTCAGCTCTTACCCTATTCTTC-3',       (SEQ ID NO 3)

R1: 5'-CACATTTTACTCCTTAACTTGGAC-3'.      (SEQ ID NO. 4)
```

A method of assisted breeding of photoperiod insensitivity in pumpkins, comprises the following steps:

1) extracting genomic DNA of the pumpkin to be tested, and detecting whether there is the presence of the TCATA deletion in the Indel molecular marker SEQ7593;

2) determining the photoperiod sensitivity in pumpkin according to the detection result, wherein, the presence of a TCATA deletion indicates that the pumpkin owns photoperiod sensitivity; whereas the absence of TCATA deletion indicates that the pumpkin owns no photoperiod sensitivity.

Application of a reagent used for detecting the presence of TCATA deletion in the Indel molecular marker SEQ7593 in the assisted breeding of photoperiod insensitivity in pumpkins.

A method of breeding of photoperiod insensitivity in pumpkins, comprises knockout of the base fragment with 5 bp in size from 129th to 133th positions of the Indel molecular marker as shown in SEQ7593 SEQ ID NO: 1 of claim 1.

The beneficial effects of the present invention are as follows:

The present invention performed the QTL mapping for the photoperiod insensitivity in pumpkins, and obtained the closely linked molecular marker SEQ7593 by screening, with a high contribution rate and an interpretation phenotypic probability of 30%. Thereby the present invention can be used for establishment of molecular marker-assisted breeding system of the photoperiod insensitivity. The PCR primer amplification designed according to Indel molecular markers can be applied to assistant breeding of pumpkin breed improvement molecules in a simple, rapid and high-throughput manner, technical support is provided for molecular breeding aimed at reducing the dependence on long-day and eliminating the restriction on sowing time or planting region, and time for conventional gene positioning is shortened greatly.

BRIEF DESCRIPTION OF THE DRAWINGS

This application contains at least one drawing executed in color. Copies of this patent or patent application publication with color drawing(s) will be provided by the Office upon request and payment of the necessary fee.

DETAILED DESCRIPTION

The present invention will be further illustrated below in conjunction with the embodiments and is not limited thereto.

The molecular biology experimental techniques used in the following embodiments comprise DNA extraction, PCR amplification, PAGE gel electrophoresis, etc., which are usually operated according to the routine procedures unless otherwise specified. The specific reference is according to Molecular Cloning Experiment Guide (third edition) (Sambrook J, Russell D W, Janssen K, Argentine J. translated by Huang Peitang et al., 2002, Beijing: Science Press), or the conditions recommended by the manufacturers.

Example 1

I. Construction of Genetical Groups and Genetic Analysis

Figure 1:
FIG. 1 shows a photoperiod insensitive female parent (PPIS) and a photoperiod sensitive male parent (PPS)

1. Materials of plants to be tested: the photoperiod insensitive and photoperiod sensitive materials were high-generation inbred lines obtained in local Guangdong province, and named as PPIS and PPS, respectively, as shown in FIG. 1. wherein the arrows indicate the locations of the female flowers (black arrows) and male flowers (white arrows) F1 was obtained by hybridization of PPIS and PPS, and F2 was obtained by selfing of F1, which were used for genetic analysis and mapping the groups.

2. Determination of the photoperiod insensitivity and analysis of inheritance of the materials to be tested.

162 Single plants of F2 groups were sowed in April, and with long-day during the flowering time. The flowering nodes of the first female flower were investigated, and the related data was processed by Excel 2016 to detect whether the data obey the normal distribution.

II. Construction of Pumpkin Genetic Map and the Preliminary Mapping of the Peel Color 1. Extraction of Genomic DNA of the Pumpkin The genomic DNA of the pumpkin parent and 160 plants of the F2 group were extracted by CTAB method, and the extracted single DNA was used for library construction.

2. Construction of Genetic Map

In the early stage of the research, Beijing Biomarker Technologies Co., Ltd. was entrusted to carry out the high-throughput sequencing by the use of the SLAF-Seq technology. A total of 162 samples were enzyme digested by HaeIII and Hpy166II, and the obtained fragments (SLAF tags) were through the process of adding A to 3' end the linkage of Dual-index sequencing joint, the PCR amplification, purification, sample mixing, gel digestion for selection of target fragment, and the performance of PE125 bp sequencing with IlluminaHiSeq™ after the library was qualified in quality inspection. The inserted fragment was 500 bp in size; the sequencing type was PE125; the actual read size was 2×100 bp after removing the label sequence for distinguishing the samples. The initial SNP set was filtered to obtain more reliable genotype data. A total of 52,246 polymorphic SLAF tags were developed, in which 4,655 high-quality SLAF tags were selected, and the tags of which MLOD values with other SLAF tags being below 5 were filtered out. Using the linkage group as the unit, the linear arrangement of Marker in the linkage group was obtained by the analysis of HighMap™ software and the genetic distance between the adjacent Markers was estimated, finally the genetic map with a total map distance of 2,502.01 cM was obtained, which were divided into 20 linkage groups, and 8,051 SNP markers in total.

3. Mapping of Photoperiod Insensitive Gene Ppd

Figure 2:
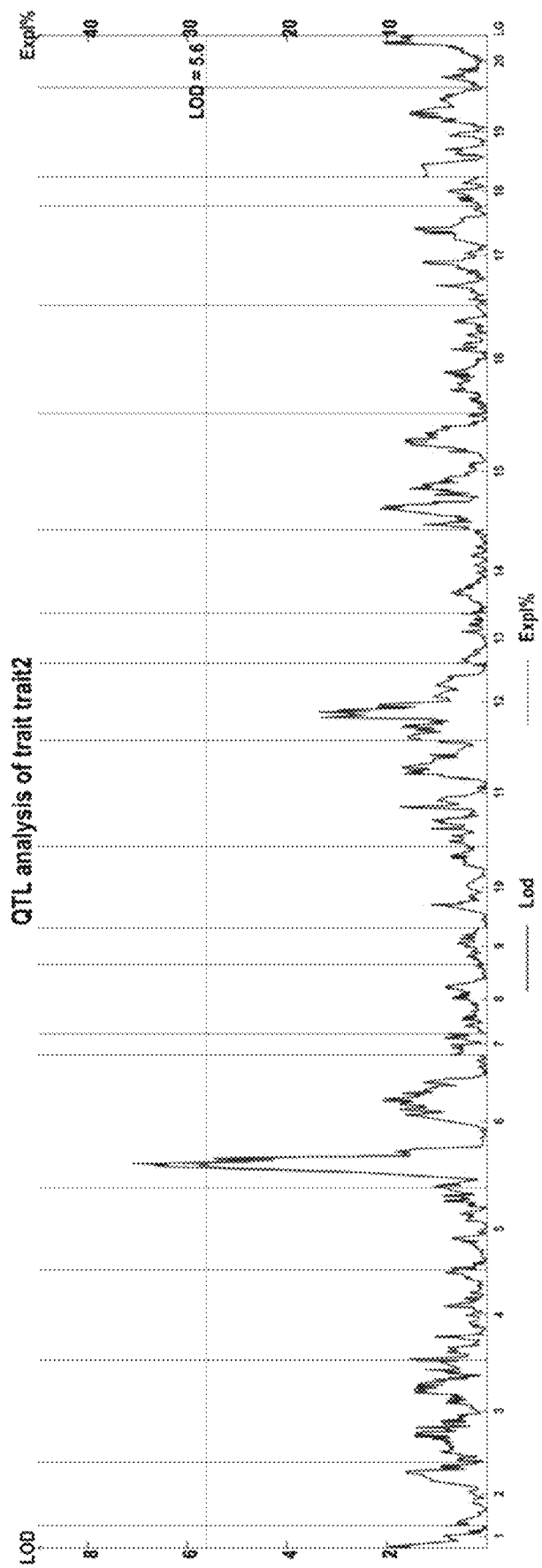
FIG. 2 shows a graph of preliminary mapping result for the pumpkin photoperiod insensitivity in the high-density genetic linkage map: the horizontal ordinate represents the position of a linkage group, and the vertical ordinate represents the LOD value; the threshold of the black line mark is the correlation threshold representing $p<0.001$, which indicates extremely reliable relevance.

The phenotypic data and the genetic map information of the groups were analyzed by Composite Interval Mapping Method (MQM) in the MapQTL™ software to obtain the trait-related QTL. The number of replacement tests was set as 1000, and the QTL standard for judgment was as follows: when the p value was less than 0.01, the corresponding LOD value was used as a threshold for screening, as indicated by the black line in the figure. Exceeding the threshold was expressed as a linkage mapping interval of one gene, the LOD value of the black line was 5.6, and one group represented one linkage group. The Ppd gene was located in the 6th linkage group (FIG. 2), ranging from 35.00 cM to 38.30 cM, the genetic distance of two markers was 3.30 cM (FIG. 2), and the markers at both ends of the interval were aligned with the *Cucurbita moschata* genome for a total of 229.3 Kb. Indel polymorphic markers were developed near the peak markers, and the Indel marker of this segment interval was obtained by complete genomic resequencing of the two parents. The insertion and deletion sites of the small fragments with a size less than 50 bp were detected by SAMTOOLS software, and was designed by premier 5.0 software according to the sequence of 200 bp in size located at the upstream and downstream of the site. The sequence of the Indel marker SEQ7593 primer was: F1:5'-TTTCAGCTCTTACCCTATTCTTC-3' (SEQ ID NO: 3), R1:5'-CACATTTTACTCCTTAACTTGGAC-3' (SEQ ID NO: 4). The PCR amplification system used a 20 μL amplification system, including 1 U Taq enzyme, 1 μL of template DNA, 1 μL of dNTP, 1.5 μL of primer, 2 μL of 10×PCR buffer, and H2O was added to 20 μL. The PCR amplification procedure was: 94° C. for 3 min, the cycle process was 94° C. for 30 s, annealing for 30 s, 72° C. for 1 min, 30 cycles, and finally extended at 72° C. for 10 min. The annealing temperature was 54° C.

Comparative analysis of the individual phenotypes and genotypes of *Cucurbita moschata* PPIS and PPS was performed, to determine that the Indel molecular marker SEQ7593 was a closely-linked marker of the photoperiod insensitivity in pumpkins and was located on tenth chromosome of *Cucurbita moschata* with the size of 280 bp, and its nucleotide sequence was shown as in SEQ. ID NO: 1.

(SEQ ID NO. 1)
TTTCAGCTCTTACCCTATTCTTCAGAGTGA

AAACCTACCCTTCAATAATTGAAGCC

-continued
TTAAACTTTAGAATTATTAGAGATTCTTTAG

AATGTTGGATAAAATTTAGTTCTGAAAT

AGTGCCAAGTTTATCATACATATGTTCTATG

TTCTAAGTTCCATCCAAAATTCTAATTG

TGCTCAAGAGTAGTTTTGAAATTTTTGTGA

AATATTGTAAATCTGATGAGAATAGATGT

ATTATTAAAACAAATCTGATGAAGTCCAAG

TTAAGGAGTAAAATGTG.

If said sequence in SEQ ID NO: 1 lacked of the fragment TCATA, e.g. the deletion of the base fragment of 5 bp in total size from the 129th to the 133th positions as shown in SEQ ID NO: 1 led to the sequence of 275 bp in size as shown in SEQ ID NO: 2, then the corresponding pumpkin exhibited photo sensitivity.

(SEQ ID NO. 2)
TTTCAGCTCTTACCCTATTCTTCAGAGTGA

AAACCTACCCTTCAATAATTGAAGCC

TTAAACTTTAGAATTATTAGAGATTCTTTAG

AATGTTGGATAAAATTTAGTTCTGAAAT

AGTGCCAAGTTTACATATGTTCTATGTTCTA

AGTTCCATCCAAAATTCTAATTGTGCTCA

AGAGTAGTTTTGAAATTTTTGTGAAATATT

GTAAATCTGATGAGAATAGATGTATTATT

AAAACAAATCTGATGAAGTCCAAGTTAAG

GAGTAAAATGTG.

Example 2

Figure 3:
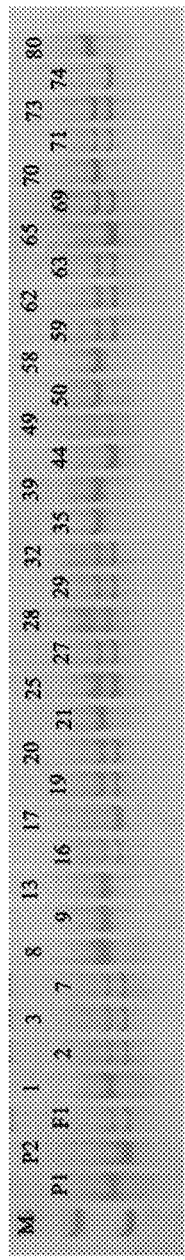
FIG. 3 shows PCR amplification results of Indel molecular marker SEQ7593: P1 and P2 represent the banding patterns of products of the photoperiod insensitive female parent and the photoperiod sensitive male parent, respectively. Wherein, the P1 amplified fragment is 280 bp in size; F1 has two banding patterns with the fragments of 280 bp and 275 bp in size, respectively, and the random single plant of F2 groups have three types of P1, P2 and F1.

PCR amplification was carried out between the two parents using the method of Example 1. The polymorphamide gel electrophoresis was used to detect the specificity between the parents. 33 Single plants of F2 groups were identified. The results were shown in FIG. 3. FIG. 3 showed the PCR amplification results of Indel molecular marker SEQ7593: P1 and P2 represented the band patterns of products of photoperiod insensitive female parent and photoperiod sensitive male parent, respectively. Wherein, P1 amplified fragment is 280 bp in size; P2 amplified fragment is 275 bp in size. F1 had two band patterns with fragments of 280 bp and 275 bp in size, and the random single plants of F2 groups had three types of P1, P2 and F1.

The phenotype of the photoperiod sensitivity was found consistent with the results of PCR on basis of the phenotype of single plants. The above-mentioned Indel molecular marker could separate the photoperiod sensitive single plants from the photoperiod insensitive ones.

The above embodiments are merely preferred examples of the present invention, and any modifications and improvements made without departing from the spirit of the invention and obvious to those skilled in the art are considered as a part of the present invention.

The invention claimed is:

1. A method of determining a photoperiod insensitivity of pumpkin, the method comprising:
extracting genomic DNA of the pumpkin to be tested, and using a primer pair to detect whether there is a presence of a TCATA deletion in an Indel molecular marker SEQ7593 at positions 129 to 133 of SEQ ID NO: 1; and determining the photoperiod sensitivity in pumpkin according to the detection result, wherein the presence of the TCATA deletion indicates that the pumpkin owns photoperiod sensitivity; whereas the absence of the TCATA deletion indicates that the pumpkin owns no photoperiod sensitivity;

wherein the Indel molecular marker SEQ7593 is closely linked to photoperiod insensitivity in pumpkins; the Indel molecular marker SEQ7593 is located on a tenth chromosome of *Cucurbita moschata*, with a size of 280 bp, and the nucleotide sequence thereof is shown as in SEQ ID NO: 1; and wherein the nucleotide sequence of the primer pair is as follows:

```
                                    (SEQ ID NO: 3)
F1: 5'-TTTCAGCTCTTACCCTATTCTTC-3',
and (SEQ ID NO: 4)
R1: 5'-CACATTTTACTCCTTAACTTGGAC-3'.
```

2. A method of breeding of photoperiod in sensitivity of pumpkins, comprising knocking out of a base fragment with 5 bp in size between positions 129 and 133 in an Indel molecular marker as shown in SEQ ID NO:1.

\* \* \* \* \*

SEQUENCE LISTING

<160> NUMBER OF SEQ ID NOS: 4

<210> SEQ ID NO 1
<211> LENGTH: 280
<212> TYPE: DNA
<213> ORGANISM: Cucurbita moschata

<400> SEQUENCE: 1
tttcagctct accctattc ttcagagtga aaacctaccc ttcaataatt gaagccttaa    60
actttagaat tattagagat tctttagaat gttggataaa atttagttct gaaatagtgc   120
caagtttatc atacatatgt tctatgttct aagttccatc caaaattcta attgtgctca   180
agagtagttt tgaaattttt gtgaaatatt gtaaatctga tgagaataga tgtattatta   240
aaacaaatct gatgaagtcc aagttaagga gtaaaatgtg                        280

<210> SEQ ID NO 2
<211> LENGTH: 275
<212> TYPE: DNA
<213> ORGANISM: Cucurbita moschata

<400> SEQUENCE: 2
tttcagctct accctattc ttcagagtga aaacctaccc ttcaataatt gaagccttaa    60
actttagaat tattagagat tctttagaat gttggataaa atttagttct gaaatagtgc   120
caagtttaca tatgttctat gttctaagtt ccatccaaaa ttctaattgt gctcaagagt   180
agttttgaaa tttttgtgaa atattgtaaa tctgatgaga atagatgtat tattaaaaca   240
aatctgatga agtccaagtt aaggagtaaa atgtg                             275

<210> SEQ ID NO 3
<211> LENGTH: 23
<212> TYPE: DNA
<213> ORGANISM: Artificial sequence
<220> FEATURE:
<223> OTHER INFORMATION: primer

<400> SEQUENCE: 3
tttcagctct accctattc ttc                                            23

<210> SEQ ID NO 4
<211> LENGTH: 24
<212> TYPE: DNA
<213> ORGANISM: Artificial sequence
<220> FEATURE:
<223> OTHER INFORMATION: primer

<400> SEQUENCE: 4
cacattttac tccttaactt ggac                                          24